United States Patent [19]

Buysch et al.

[11] Patent Number: 4,897,436

[45] Date of Patent: Jan. 30, 1990

[54] NEW STABILIZERS AND THEIR USE FOR THE PRODUCTION OF STABILIZED POLYAMIDES AND RUBBER MATERIALS

[75] Inventors: Hans-Josef Buysch, Krefeld; Zsolt Szentivanyi, Leverkusen; Bert Brassat; Christiane Oppenheimer-Stix, both of Krefeld, all of Fed. Rep. of Germany

[73] Assignee: Bayer Aktiengesellschaft, Leverkusen, Fed. Rep. of Germany

[21] Appl. No.: 141,960

[22] Filed: Jan. 11, 1988

[30] Foreign Application Priority Data

Jan. 22, 1987 [DE] Fed. Rep. of Germany ....... 3701738

[51] Int. Cl.$^4$ .............................................. C08K 5/34
[52] U.S. Cl. ...................................... 524/83; 544/35; 544/38
[58] Field of Search ....................... 524/83; 544/35, 38

[56] References Cited

U.S. PATENT DOCUMENTS 3,909,448  9/1975  McGuigan et al. ................... 524/83
4,430,452  2/1984  Buysch et al. ....................... 521/107

FOREIGN PATENT DOCUMENTS 36544  4/1978  Japan .................................... 524/83
932066  7/1963  United Kingdom ................. 524/83

Primary Examiner—John Kight
Assistant Examiner—Kriellion Morgan
Attorney, Agent, or Firm—Connolly and Hutz

[57] ABSTRACT

Products prepared by reacting isopropenyl phenols or bisphenols of the bisphenol-A type with diphenyl amine, phenothiazin or derivatives thereof in the presence of acidic catalysts are used as stabilizers for polyamides and rubbery materials.

8 Claims, No Drawings

NEW STABILIZERS AND THEIR USE FOR THE PRODUCTION OF STABILIZED POLYAMIDES AND RUBBER MATERIALS

This invention relates to new stabilizers or stabilizer mixtures which are obtained by reaction of isopropenyl phenols or bisphenols of the bisphenol A type with diphenyl amine or phenothiazine or derivatives of these compounds in the presence of acidic catalysts and which may optionally be further modified with oxiranes, aldehydes and other compounds. The invention also relates to the use of these new stabilizers or stabilizer mixtures for the production of correspondingly stabilized polyamides and rubber materials.

Diphenylamine derivatives with phenol nuclei attached thereto are known in principle. U.S. Ser. No. 3,673,091 describes diphenylamines corresponding to the following formula

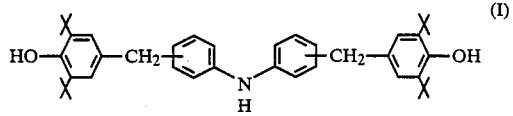
(I)

prepared from diphenylamine and 4-hydroxy-3,5-di-tert.-butyl benzylalcohol which are used as antioxidants for lubricating oils. However, their oxidation-inhibiting effect in other substrates, such as polyamides, is only moderate or totally inadequate.

It has now surprisingly been found that reaction products according to the invention of isopropenyl phenols or bisphenols with diphenylamine, phenothiazine or derivatives of these compounds are excellent antioxidants for polyamides and rubber materials.

It is particularly surprising that products of this type even if they do not contain any polymerizable functions, behave like bound stabilizers in rubber and, accordingly, retain their effect for longer than standard antioxidants, even under extractive conditions.

Bound antioxidants are chemically fixed to the polymer matrix by holding groups such as for example, the nitroso, sulfhydryl, vinyl, allyl and acryl group. Antiagers of this type are described in DE-A No. 2 735 178, DE-A No. 2 509 654, DE-A No. 3 022 952, DE-A No. 2 025 336, DE-A No. 3 113 351 and U.S. Ser. No. 3,867,334.

On the one hand, the antiagers according to the invention retain their excellent protective effect, even under extractive ageing conditions, in the absence of holding groups On the other hand, however, it is also possible to provide them with such holding groups, as shown further below.

Suitable starting materials for the production of the formula (II) below and phenothiazines corresponding to general formula (III)

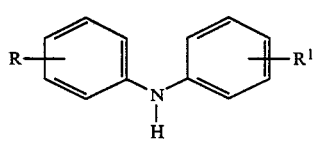
(II)

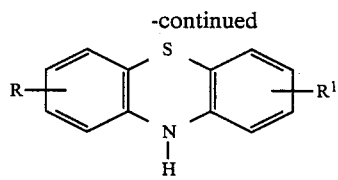
(III)

in which R and $R^1$, which may be the same or different and are in the ortho, meta and/or para position to the N-atom, represent $C_1$–$C_8$ alkyl, $C_7$–$C_{10}$ aralkyl, OH groups or Cl atoms, preferably $CH_3$, $C_2H_5$, tert.-butyl, isooctyl, styryl or OH groups, but more preferably hydrogen, and also groups corresponding to the following formula

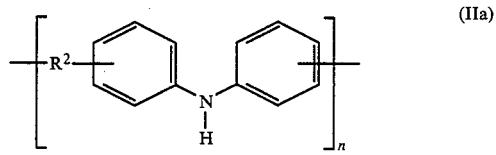
(IIa)

or to the following formula

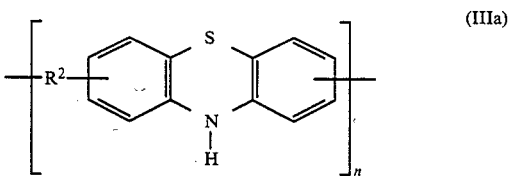
(IIIa)

in which
$R^2$ is a double-bonded radical

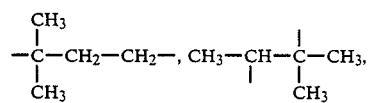

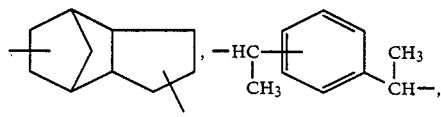

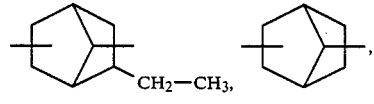

preferably

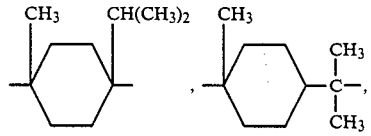

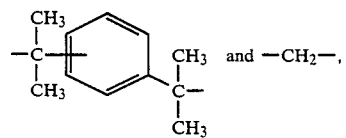

the groups (IIa) and (IIIa) being attached to the groups (II) and (III) by $R^2$, and n is an integer of from 1 to 5 and preferably of from 1 to 3.

Starting materials having the structures (IIa) and (IIIa) and their production are described in EP No. 70 436. However, compounds corresponding to formulae (II) and (III) are preferably used, diphenylamine and phenothiazine being particularly preferred.

Suitable phenolic starting compounds are isopropenyl phenols corresponding to the following formula

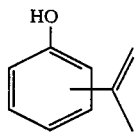
(IV)

in which the isopropenyl groups may be in the o-, m-position, but preferably in the p-position to the OH group, or bisphenols corresponding to the following formula

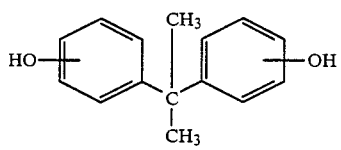
(V)

in which the OH groups are in the o-, m-, but preferably p-position to the isopropylidene group. It is also possible to use the resin obtained in the production of bisphenol A which, after crystallization and separation of bisphenol A, is obtained as residue of the mother liquor and still contains relatively large quantities of bisphenols corresponding to formula (V).

The reaction of diphenylamines corresponding to formula (II) or phenothiazines corresponding to formula (III) with isopropenyl phenols (IV) or bisphenols (V) in the process according to the invention takes place in the presence of an acidic catalyst in the melt or in solvents (inert under the reaction conditions) at temperatures of from 100° to 300° C., preferably at temperatures of from 130° to 260° C. and more preferably at temperatures of from 150° to 250° C.

Suitable solvents are aliphatic or aromatic hydrocarbons, aromatic halogen compounds or ethers. Examples of suitable solvents are isooctane, cyclohexane, decane, toluene, xylene, mesitylene, chlorobenzene, dichlorobenzene, diphenylether. It is best to use solvents which are not volatile under the reaction conditions, so that the reaction does not have to be carried out in pressure vessels.

The reaction components amine and phenol are used in a molar ratio of from 0.1:1 to 2:1, preferably in a molar ratio of from 0.3:1 to 1.5:1 and more preferably in a molar ratio of from 0.4:1 to 1:1.

Suitable catalysts are those which have a $pK_{acid}$-value, as measured in water, of less than 3. Examples of suitable catalysts are, for example, hydrochloric acid, phosphoric acid, phosphorous acid, sulfuric acid, methanesulfonic acid, p-toluenesulfonic acid, methanephosphonic acid, benzene-phosphonic acid, aluminium chloride, boron fluoride and adducts thereof, such as boron fluoride etherate, boron trichloride. Acidic aluminium silicates, such as zeolites, and acid-activated layer silicates of the bentonite and montmorillonite type, are also suitable catalysts.

Where compounds corresponding to formula (V) are used as starting materials, phenol is formed during the reaction and is best distilled off either during the reaction or on completion thereof.

The reaction products are obtained as crystalline or resinous, often brittle, brown-colored residues after removal of the solvent used, if any, and the phenol formed, if any, by distillation. The residues naturally consist mostly of several chemical individuals which, for example in the reaction of diphenylamine or phenothiazine with isopropenyl phenol, correspond in parts to formulae (VI) and (VII) below:

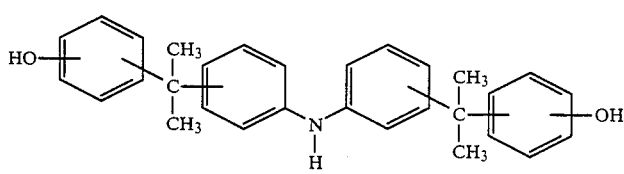
(VI)

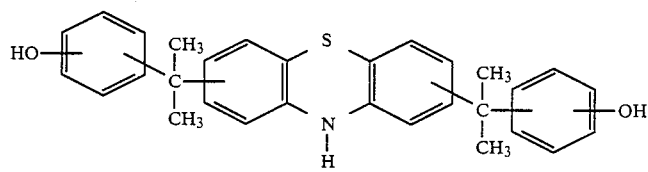
(VII)

The primary reaction products, represented for example by (VI) and (VII), may be further modified by reaction with compounds corresponding to the following formula $$X{-}[R^3{-}Y]$$ (VIII)

in which

X and Y may be the same or different and represent H, OH, halogen (particularly Cl or Br), an ethylene, propylene or oxirane group; one of the two substituents or the bracketed expression may even be H with the proviso that, in this case, X is neither OH nor halogen; in addition, X may represent —CH=O where the group in brackets is aliphatic and contains from 1 to 4 carbon atoms, $R^3$ is a single-or double-bonded aromatic radical or a single- or double-bonded aliphatic radical containing from 1 to 12 carbon atoms which may contain one or more OH, ether, thioether, carbonyl, ester groups and double bonds and also aromatic nuclei containing from 6 to 12 carbon atoms; this reaction may take place both at the OH groups and at the aromatic nuclei of the primary reaction products.

Preferably, X and Y represent H, OH, halogen, ethylene, propylene, oxirane; in addition, X represents —CH=O where the expression in brackets is H or CH$_3$, R$^3$ is a single- or double-bonded aromatic radical containing 6 carbon atoms or a single- or double-bonded aliphatic radical containing from 1 to 9 carbon atoms which may contain 1 or 2 ether, ester groups and/or double bonds and also aromatic nuclei containing 6 carbon atoms.

More preferably, X and Y represent H, halogen, oxirane; in addition X represents —CH=O where the bracketed expression is hydrogen and R$^3$ represents a single- or double-bonded aliphatic radical containing from 1 to 6 carbon atoms.

Suitable starting materials corresponding to formula (III) are, for example, aldehydes, such as formaldehyde, acetaldehyde, isobutyraldehyde, alkyl halides, such as allyl chloride, methallyl bromide, methylene chloride, 1,4-dichloro-2-butene, benzyl chloride, xylylene dichloride, dichloroethane, dibromohexane; alcohols, such as isopropanol, tert.-butanol, amyl alcohol, α-hydroxyethylbenzene, α-hydroxycumeme, α,α'-dihydroxydiisopropylbenzene; olefins, such as propene, butene, isobutene, isoprene, 2,5-dimethyl-1,5-hexadiene, divinylbenzene, diisopropenylbenzene, ethyl acrylate, methyl methacrylate, glycol dimethacrylate, glycol diacrylate, methylvinylketone, carboxylic acid chlorides, such as acetyl chloride, acrylic acid chloride, methacrylic acid chloride, fumaric acid dichloride, adipic acid dichloride, terephthalic acid dichloride, 4-thiaheptanedioic acid dichloride, 3-oxapentanedioic acid dichloride, 4,5-dithiaoctanedioic acid dichloride, oxiranes, such as ethylene oxide, propylene oxide, glycidol, epichlorohydrin, diglycidol, bisphenolbisglycidylether, vinyl ethylene oxide, N,N-bisglycidyl aniline and hexahydrophthalic acid bisglycidyl ester.

Preferred starting compounds of formula (III) are formaldehyde, allyl chloride, 1,4-dichloro-2-butene, benzylchloride, tert.-butanol, α-hydroxycumene, α,α'-dihydroxyisopropylbenzene, isobutene, diisopropenylbenzol, (meth)acrylic acid chloride. Oxiranes, such as ethylene oxide, propylene oxide and epichlorohydrin, are particularly preferred.

The reaction with the compounds corresponding to formula (VIII) is carried out by standard methods. Alkylation reactions with alcohols or olefins in the presence of strong acids at elevated temperature, alkylation or acylation reactions with halogen compounds by simple heating or in the presence of equimolar quantities of bases to form a phenolate of high reactivity from the phenolic OH and to bind the acid released (cf. Houben-Weyl, Methoden der organischen Chemie 6/1c, pages 925 et seq. and VIII, pages 543 et seq.).

Where activated olefins, such as acrylates, are used, a catalytic quantity of base is sufficient for the alkylation of the phenolic OH group by Michael addition. The same also applies to the base-catalyzed addition of oxiranes to the phenolic OH group (Houben-Weyl, Methoden der Organischen Chemie, Vol. 6/3, pages 49 et seq., 79 et seq. and 6/1c, pages 999 and 1081; 6/3, pages 71 et seq. and Rodds Chemistry of Carbon Compounds, Vol. III E, 158 et seq., Elsevier Publ. Co. Amsterdam, 1974) and Organic Reactions, Vol. 10, pages 179 et seq., John Wiley and Sons, 1959).

The compounds obtained from starting compounds (VI) and (VII) are shown by way of example in the following:

The compound obtained with a single-bonded radical R$^3$ corresponds for example to the following formula:

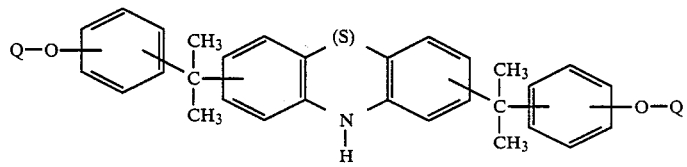

in which Q may be

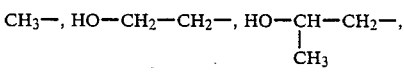

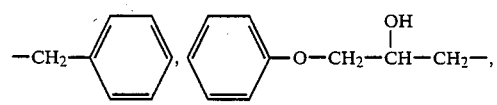

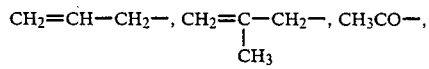

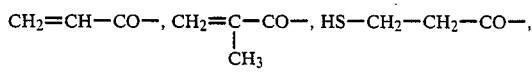

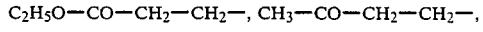

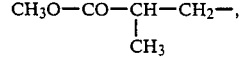

or to the following formula

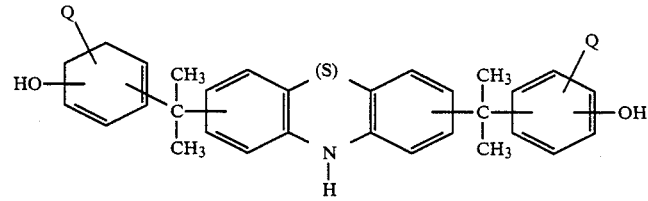

in which Q may be

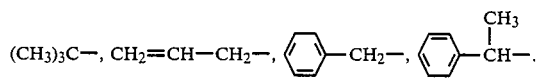

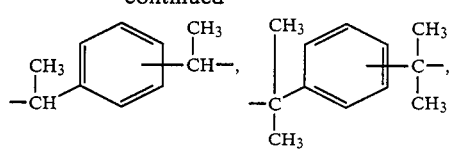

The compound obtained with a double-bonded radical R³ corresponds for example to the following formula

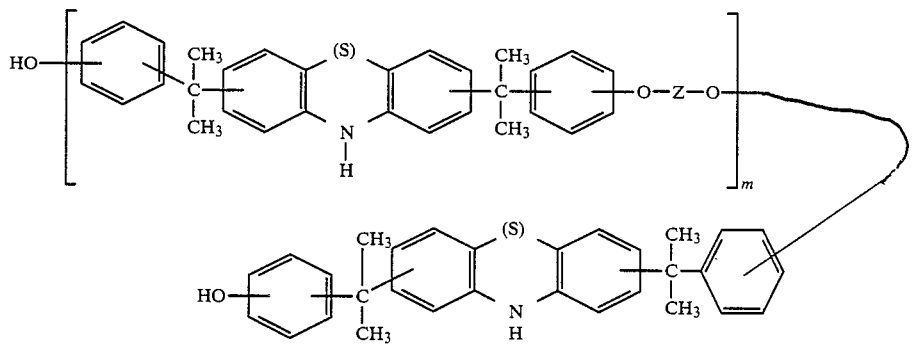

in which Z may be

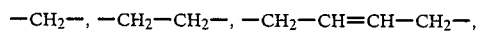

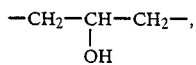

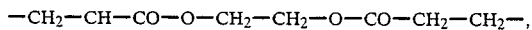

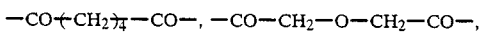

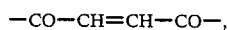

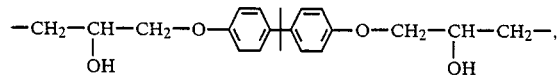

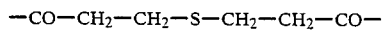

or to the following formula

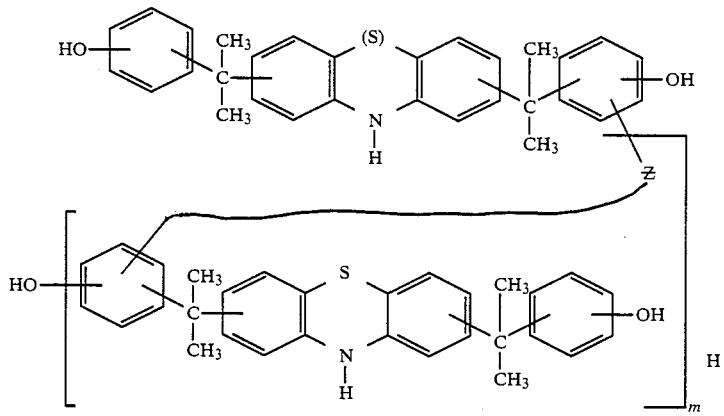

in which Z may be

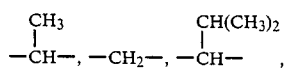

and m is an integer of from 1 to 15 and preferably of from 1 to 10.

The present invention also relates to the further reaction products obtained by these reactions of the primary reaction products with compounds corresponding to formula (VIII).

In general, there is no need for the primary reaction products or the further reaction products to be worked up by particular methods. In general, it is sufficient to remove the catalyst and to distill off volatile constituents. The sump product may be used as such or, in certain cases, may be purified by precipitation or recrystallization from suitable solvents.

Both the reaction products of the diphenylamines (II) and phenothiazines (III) as such and their modified derivatives as described above are used as excellent stabilizers for polyamides and rubbers and products containing polyamides and rubbers.

They are used in stabilizing quantities of from 0.1 to 10% by weight, preferably from 0.2 to 6% by weight and more preferably from 0.3 to 5% by weight, based on the substrates to be stabilized.

Synthetic polyamides of the type obtained by polycondensation of diamines with dicarboxylic acids, by polymerization of lactams or by polycondensation of aminocarboxylic acids may be stabilized with the stabilizers according to the invention. Aliphatic polyamides, particularly those of adipic acid and hexamethylenediamine or of caprolactam, and copolyamides of the type in which the last-mentioned components are the principal constituents are preferably stabilized with the stabilizers according to the invention.

Polymaides containing polymeric or rubber-like modifiers, of the type known in large numbers in the prior art for improving toughness, may also be stabilized with advantage.

The stabilizers may be incorporated both before or during and also after polymerization, being used either as such or in the form of a solution in an inert solvent or one of the polyamide-forming starting materials or in the form of a concentrate in a suitable polymer, preferably in polyamide. The stabilizers are preferably incorporated in the polyamide melt using known mixing units, such as extruders, kneaders, static mixers and stirrers. It is also possible to add to the polyamides various additives of the type normally used, including lubricants and mold release agents, nucleating agents, pigments, dyes, reinforcing or non-reinforcing fillers, such as mineral fibers, glass and asbestos fibers, microspheres of glass, nucleating agents, such as talcum, silicon oxide or mica, antistatic agents, plasticizers and UV stabilizers.

The polyamides stabilized by the process according to the invention are eminently suitable for the production of industrial rayon for fishing nets, drive belts, conveyor belts, tire cord or moldings which are exposed to thermal stressing in the presence of air or oxygen. They are also emiinently suitable in the form of wires, for example, for bracing wires in fruit growing or viniculture or for pasture hedging.

Providing they contain groups suitable for radical attachment, the new antiagers may be attached to polymers in several ways, namely during the radical polymerization of the monomers mentioned below, preferably by grafting onto preformed polymers, but more preferably during the hardening and vulcanization of the polymers.

These reactions are carried out in known manner by mass, emulsion, solution or dispersion polymerization in the presence of the compounds (I), while hardening or vulcanization is carried out under the usual conditions in the presence of known hardening and vulcanization systems.

The antiagers according to the invention may be reacted with vinyl monomers in known manner to form copolymers having molecular weights of from 1000 to 30,000 and a high content of from 5 to 70% by weight and preferably from 10 to 60% by weight of (I).

In addition, the antiagers (I) may also be grafted onto polymers having molecular weights of from 1000 to 30,000 (number average) and preferably from 2000 to 20,000, so that the polymers have a content of bound antiager of from 10 to 60% by weight and preferably from 10 to 50% by weight. Such compounds are then added to the high molecular weight polymers and likewise form migration-resistant, non-extractable, effective polymeric antiagers. They are added to the high molecular weight polymers in such quantities that the above-mentioned concentrations of antiager are maintained throughout the polymer. To this end, the low molecular weight polymers containing the antiager in bound form are used in quantities of from 1 to 25% by weight and preferably in quantities of from 4 to 20% by weight, based on the high molecular weight polymers.

Suitable low molecular weight polymers for such graft reactions are, for example, polybutadienes, polyisoprenes, copolymers of butadiene and/or isoprene with styrene, acrylonitrile, methyl methacrylate, ethyl acrylate, o-methyl styrene, piperylene, 1,3-hexadiene, ethylene, propylene and vinyl acetate or corresponding graft rubbers.

Suitable vinyl monomers for the production of the copolymers are those mentioned above.

The grafting of the antiagers onto the polymers takes place under radical conditions, for example in the presence of known radical initiators, such as tert.-butyl perpivalate, dicumyl peroxide, di-tert.-butyl peroxide or azodiisobutyronitrile, either without dilution or in inert solvents, such as toluene, xylene, gasoline, chlorobenzene or dichlorobenzene, at temperatures of from 50° to 200° C. and preferably at temperatures of from 70° to 180° C.

The new antiagers are equally suitable for a broad range of rubbers and plastics, but more especially for rubbers, for example for polymers of 1,3-dienes, such as butadiene, isoprene, piperylene, 2-chlorobutadiene and/or 2-ethyl butadiene and copolymers thereof with vinyl monomers, such as styrene, p-methyl styrene, α-methyl styrene, norbornene, norbornadiene, acrylic acid, acrylic acid esters and amides, acrylonitrile, ethylene, propylene and vinyl acetate, for polyalkenamers, for example of cyclopentene or 1,5-cyclooctadiene, and for polymers of 1-olefin mixtures, for example of ethylene/propylene or ethylene/propylene/diene containing isolated double bonds. Polymers such as these may be produced by radical, coordinative, metathetic or ionic polymerization.

Examples of such polymers are BR, natural rubber, SBR, NBR, EPDM and CR rubber, polypentenamer, also polyethylene, polypropylene or polystyrene with low double bond contents and, finally, single-phase or multiphase polymer mixtures, such as ABS or polystyrene, polyethylene, polypropylene, but preferably polymers containing double bonds.

The antiagers are particularly effective in nitrile rubber.

The rubbers may be vulcanized.

Elongation at break may be further improved by addition of from 5 to 15% by weight, based on rubber solids, of oligomeric thioethers, for example ether thioethers, such as Vulcanol 85 ®, a product of Bayer AG, Leverkusen.

Antiagers according to the invention, which do not contain any particular holding groups suitable for fixing to the polymer matrix, are incorporated in the polymers in the usual way by means of kneaders, mixing rolls, screw mixers and extruders, after which the polymers may be vulcanized.

EXAMPLE 1

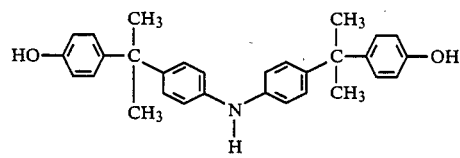

A mixture of 338 g (2.0 moles) diphenylamine, 268 g (1.0 mole) dimeric p-isopropenylphenol and 20 g Tonsil ® Optimum(acid-activated montmorillonite of Süd-chemie, München) is heated for 2 h to 150° C., diluted with xylene and feed from the catalyst by filtration under pressure. After concentration of the filtrate by evaporation to a sump temperature of 190° C./1 mbar, 572 g of a light brown, brittle resin are obtained which, after recrystallization from xylene/ligroin(5:1), gives a crystalline product melting at 136° to 142° C. which largely corresponds to the above formula.

EXAMPLE 2

A mixture of 386 g (2.28 moles) diphnylamine, 1043 g (4.58 moles) bisphenol A and 40 g Tonsil ® Optimum is melted under nitrogen. The melt is then heated with stirring to 150° C. and the pressure reduced to 10–20 mbar. Phenol then begins to distill off slowly through an approximately 50 cm long metallized Vigreux column. As the phenol distills off, the sump temperature is increased to 195° C. The reaction is over after 17–20 h, by which time 445 g phenol have distilled over. The residue is diluted with toluene, freed from the catalyst by filtration under pressure, the filter cake is washed with toluene and the combined filtrates are concentrated by evaporation at approximately 20 mbar up to a sump temperature of 170° C. 963 g of a brown brittle resin containing 7.7% by weight phenolic OH (calculated 7.2%, based on formula VII with R and $R^1$=H) are obtained.

EXAMPLE 3

A mixture of 199 g (1.0 mole) phenothiazine, 456 g (2.0 moles) bisphenol A and 20 g Tonsil ® Optimum is reacted as in Example 2. 181 g phenol distills off over a period of 14 h up to a sump temperature of 205° C./15 mbar. Working up as in Example 2 gives 454 g of brown, brittle resin containing 7.1% phenolic OH.

EXAMPLE 4

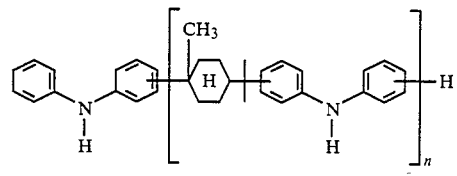

1352 g (8 moles) diphenylamine and 50 g acid-activated alumina are heated with stirring under nitrogen to 100° C., followed by the addition of 194 g (1 mole) α,α'-dihydroxy-p-diisopropylbenzene. The mixture is heated to 150° C., the water of reaction distilling off. After 1 h at 150° C., the mixture is heated for 30 minutes to 170° C., filtered through a pressure filter and excess diphenylamine distilled off from the clear filtrate at 1–2 mbar. The sump product is taken up in hot xylene. A crystalline product melting at 170°–180° C. is obtained on cooling.

(b) A mixture of 164 g (0.33 mole) of the product from (Example 4a), 151 g (0.66 mole) bisphenol A and 10 g Tonsil ® Optimum is reacted in 12 h as in Example 2, 63 g phenol distilling off. Working up leaves 251 g of a brown brittle resin.

EXAMPLE 5

(a) A mixture of 338 g (2 moles) diphenylamine, 136 g (1 mole) limonene and 20 g Tonsil ® Optimum is kept at 200° C. for 10 h, freed from catalyst by filtration under pressure and then from excess starting products by distillation at approximately 1 mbar up to a sump temperature of 200° C. 331 g of a yellow, soft resin are obtained. According to analysis, this resin has the following idealized structure:

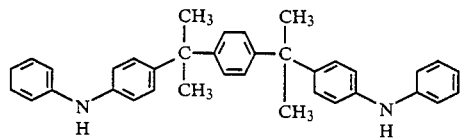

with n=substantially 1–5.

(b) A mixture of 196 g of the product of Example 5a), 190 g bisphenol A and 15 g Tonsil ® Optimum is reacted as in Example 2, 73 g phenol being distilled off. Working up leaves 290 g of a yellow-brown resin.

EXAMPLE 6

220 g (approximately 0.5 mole) of the product of Example 2 are dissolved in ethanol. After the addition of 15 g concentrated hydrochloric acid, 27 g 37% strength (by weight) formalin solution are introduced dropwise with stirring under nitrogen after 6 h at 100°, the reaction mixture is mildly alkalized with ammonia solution. After dilution with toluene, the reaction mixture is washed free from salt with water and concentrated by evaporation at 20 mbar up to a sump temperature of 170° C. 205 g of a brittle resin are obtained.

EXAMPLE 7

220 g (approximately 0.5 mole) of the product of Example 2 are dissolved in isopropanol with 20 g (0.5 mole) NaOH and the resulting solution heated with stirring under nitrogen to boiling temperature. 47 g (0.5 mole) epichlorohydrin are added dropwise over a period of about 30 minutes, followed by refluxing for another 7 h. isopropanol is then distilled off in such a quantity that the sump temperature rises to 135° C., being kept at that level for 3 h. After filtration under pressure to remove the salt precipitated (approximately 30 g), the filtrate is concentrated by evaporation at 20 mbar up to a sump temperature of 170° C. A brittle resin is obtained (241 g), corresponding to the following idealized structure:

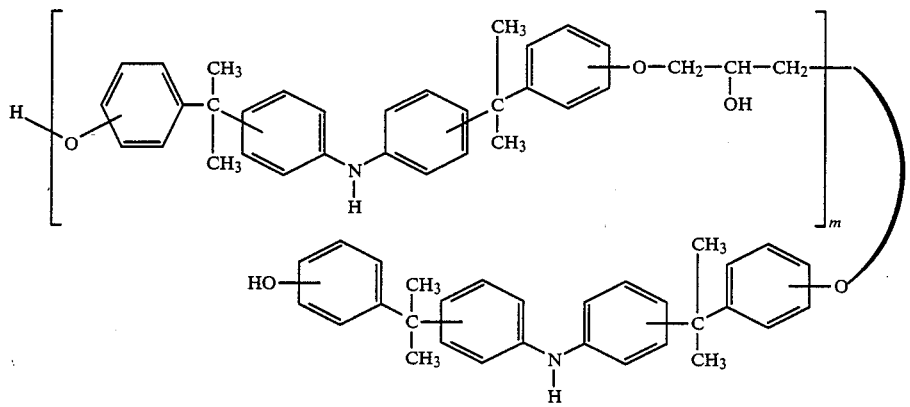

EXAMPLE 8

200 g (approximately 0.46 mole) of the product of Example 2 are dissolved in ethanol with 40 g (1.0 mole) NaOH and the resulting solution heated with stirring under nitrogen to boiling temperature, followed by the dropwise addition at approximately 30° C. of 75 g (0.975 mole) allyl chloride. After another 10 h at 78° C., the salt precipitated is isolated by filtration under suction, the salt (approximately 58 g) is digested with ethanol and, after dilution with toluene, the combined filtrates are washed with water until completely free from salt and concentrated by evaporation at 10 mbar to a sump temperature of 100° C. 225 g of a highly viscous, light brown resin are obtained which, after analysis, is reacted to the O-allyl ether of the product of Example 2 and (partly) corresponds to the following idealized structure:

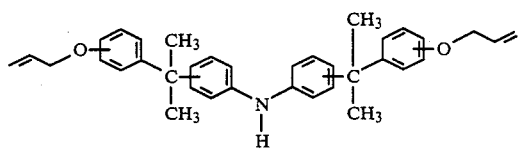

COMPARISON EXAMPLE 1

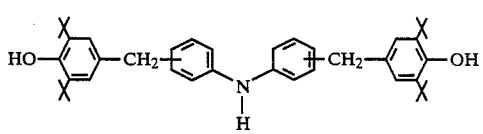

According to Example 2 of U.S. Ser. No. 3,673,091.

COMPARISON EXAMPLE 2

Instead of diphenylamine, phenothiazine is reacted with 4-hydroxy-3,5-di-tert.-butyl benzylalcohol (see also Comparison Example 1).

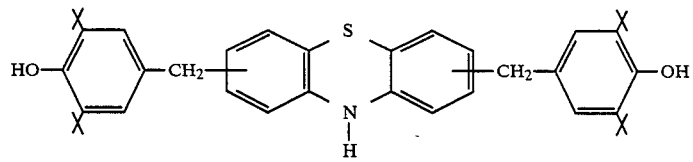

Testinq of the stabilizer effect in polyamide-6

To test the stabilizer effect, the substance to be tested is homogeneously incorporated in polyamide-6 ($\eta_{rel}=4.0$) in a concentration of 0.5% by weight by passage through an extruder. The material thus stabilized was injection-molded to form standard small test bars and subjected to thermal ageing in air at 150±0.5° C. After 1, 2, 4, 8 days, etc., 8 standard small test bars were removed and, after cooling for 2 hours in an exsiccator, were tested for impact strength in accordance with DIN 53 453. The test is passed if at least half the test specimens are unbroken or if the average impact strength of the broken test bars is above 30 kJ/m². The stabilizer effect is evaluated by a stage classification in accordance with the following Table:

| | days | | | | |
|---|---|---|---|---|---|
| Thermal ageing time to failure of impact test | 1 | 2 | 4 | 8 | 16 etc. |
| Effectiveness stage of the stabilizer | 0 | 1 | 2 | 3 | 4 |

The test results of the stabilizers according to the invention are shown in Table I and those of the comparison stabilizers in Table II.

TABLE I

| Stabilizer of Example no. | Effectiveness stage |
|---|---|
| 1 | 4–5 |
| 2 | 5 |
| 3 | 4 |
| Comparison Examples | |
| 1 | 1–2 |

TABLE I-continued

| Stabilizer of Example no. | Effectiveness stage |
|---|---|
| 2 | 1-2 |

In every case, the stabilizers according to the invention are superior in their effectiveness to the compounds according to U.S. Ser. No. 3,673,091.

Testing of the stabilizer effect in NBR rubber

An NBR rubber of 72% by weight butadiene and 28% by weight acrylonitrile was vulcanized in accordance with the following formulation in the presence of antiagers according to the invention and known antiagers:

100.0 parts by weight NBR
1.5 parts by weight mecaptosilane
30.0 parts by weight precipitated silica
0.75 part by weight stearic acid
3.0 parts by weight zinc oxide
2.5 parts by weight of a mixture of fatty acid and fatty acid esters
30.0 parts by weight kaolin, calcined
0.2 part by weight sulfur granulate, 80%
2.5 parts by weight tetramethyl thiuram disulfide
2.0 parts by weight dibenzothiazyl disulfide
2.0 parts by weight mercaptobenzthiazole, zinc salt
2.0 parts by weight antiagers A-D
A=distyryl diphenylamine standard commercially available non-bound antiager (for comparison)
B=antiager of Example 2
C=antiager of Example 8
D=antiager of Example 7

| | Comparison | Stabilization in accordance with the invention | | |
|---|---|---|---|---|
| | A | B | C | D |
| Mooney scorch 120° C. (mins.) | 14.0 | 14.0 | 14.0 | 14.0 |
| Vulkameter $t_{10}$ (mins.) | 2.8 | 2.8 | 2.7 | 2.7 |
| 170° C. $t_{10}$ (mins.) | 4.2 | 4.2 | 4.1 | 4.1 |
| Vulcanization 20' 170° C. hot-air ageing at 135° C. in a cell oven | | | | |
| Residual elongation at break % after 7 days | 82 | 92 | 96 | 80 |
| Residual elongation at break % after 11 days | 64 | 72 | 67 | 63 |
| Ageing in fuel C 48 h 40°, redrying 48 h 40° C. in vacuo, hot air ageing at 135° C. | | | | |
| Residual elongation at break % after 7 days | 78 | 85 | 87 | 75 |
| Residual elongation at break % after 11 days | 65 | 87 | 77 | 73 |

The Table clearly shows:
(a) In the hot air ageing test at 135° C., antiagers B and C according to the invention are considerably superior in their effect to the commercially available product A hitherto regarded as highly effective. Antiager D is comparable with A.
(b) After extractive treatment (fuel), followed by ageing, all the antiagers according to the invention are superior to the comparison antiager, compound B being particularly resistant to extractive ageing although it does not have any holding groups to anchor it in the polymer substrate.

We claim:

1. Reaction products of diphenylamines corresponding to general formula (II) and phenothiazines corresponding to general formula (III) below

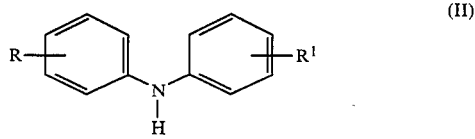

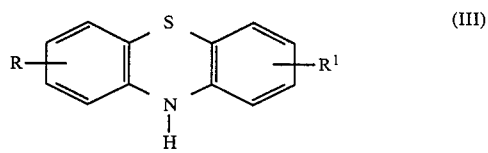

in which
R and $R^1$, which may be the same or different and are in the o-, m and/or p-position to the N-atom, represent hydrogen, $C_1$-$C_{18}$ alkyl, $C_7$-$C_{10}$ aralkyl, OH, Cl, a group corresponding to the following formula

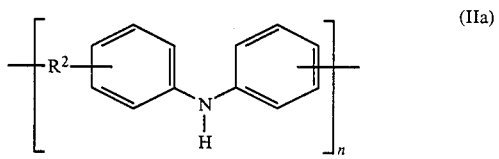

or a group corresponding to the following formula

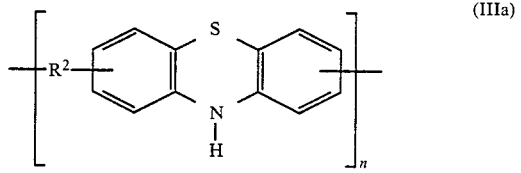

in which
$R^2$ is one of the following groups

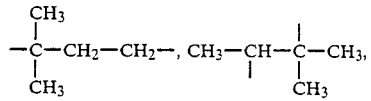

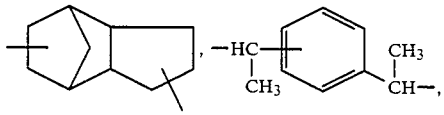

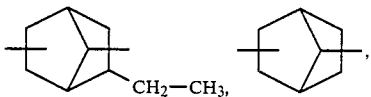

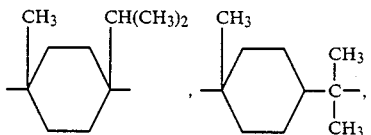

-continued

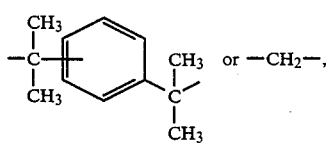

the groups (IIa) and (IIIa) being attached to the groups (II) and (III) by $R^2$, and n is an integer of from 1 to 5, with isopropenyl-phenols corresponding to the following general formula

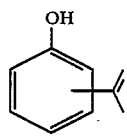 (IV)

in which the OH group is in the o-, m- or p-position to the isopropenyl group, or bisphenols corresponding to the following formula

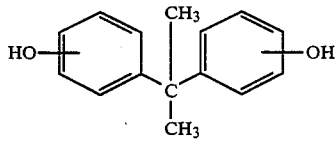 (V)

in which the OH groups are in the ortho, meta and/or para position to the isopropylidene group, which are obtained by reaction of amines (II) and/or (III) with phenols (IV) and/or (V) in a molar ratio of from 0.1:1 to 2:1 in the presence of acid catalysts at temperatures of from 100° to 300° C., and, optionally, are additionally modified by further reaction with compounds corresponding to the following general formula $$X-R^3-Y]$$ (VIII)

in which

X and Y may be the same or different and represent H, OH, halogen, an ethylene, propylene or oxirane group; one of the two substituents or the expression in brackets may be H with the proviso that, in this case, X is neither OH nor halogen, in addition to which X may be —CH═O if the expression in the square brackets is an aliphatic group containing from 1 to 4 carbon atoms, $R^3$ is a single- or double-bonded aromatic radical or a single- or double-bonded aliphatic radical containing from 1 to 12 carbon atoms which may contain one or more OH, ether, thioether, carbonyl, ester groups and/or double bonds and aromatic nuclei containing from 6 to 12 carbon atoms; this reaction may take place both at the OH groups and at the aromatic nuclei of the primary reaction products.

2. Reaction products of (II) and (III) as claimed in claim 1 in which R and $R^1$ are H, $CH_3$, $C_2H_5$, tert.-butyl, isooctyl, OH or a group of the formula (IIa) or (IIIa), in which $R^2$ is

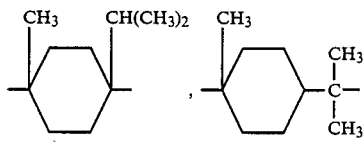

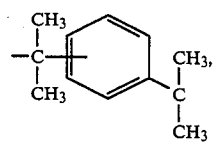

or —$CH_2$—, the groups (IIa) and (IIIa) being attached to the groups (II) and (III) by $R^2$, and n is an integer of from 1 to 3, with isopropenylphenols or bisphenols corresponding to formula (V) and optionally modified by further reaction with X—($R^3$—Y) (VIII), in which X and Y═H, halogen, OH, ethylene, propylene and oxirane, in addition to which X is —HC═O where the expression in brackets is H or $CH_3$, $R^3$ is a single- or double-bonded aromatic radical containing 6 carbon atoms or a single- or double-bonded aliphatic radical containing from 1 to 9 carbon atoms which may contain 1 or 2 ether, ester groups and/or double bonds and aromatic nuclei containing 6 carbon atoms.

3. Reaction products s claimed in claim 1 of diphenylamine and phenothiazine with isopropenylphenols (IV) or bisphenols (V), in which the OH groups are in the p-position to the isopropenyl groups or to the isopropylidene groups and optionally modified by further reaction with (VIII), in which X and Y are H, halogen, oxirane, in addition to which X is —CH═O where the expression in brackets is H, $R^3$ is a single- or double-bonded aliphatic radical containing from 1 to 6 carbon atoms.

4. The use of the reaction products claimed in claim 1 in stabilizing quantities of from 0.1 to 10% by weight, preferably of from 0.2 to 6% by weight and more preferably of from 0.3 to 5% by weight for stabilizing polyamides or rubbers and rubber-containing materials.

5. Polyamides containing stabilizing quantities of from 0.1 to 10% by weight of the reaction products claimed in claim 1.

6. Polyamide-6 and polyamide-66 containing stabilizing quantities of from 0.1 to 10% by weight and preferably of from 0.2 to 6% by weight of the reaction products claimed in claim 1.

7. Rubber and rubber-containing materials containing from 0.1 to 10% by weight and preferably from 0.2 to 6% by weight of the reaction products claimed in claim 1.

8. Rubbers as claimed in claim 7, characterized by the use of NBR rubber containing stabilizing quantities of from 0.1 to 10% by weight and preferably of from 0.2 to 6% by weight of the reaction products claimed in claim 1.

* * * * *